US009031659B2

(12) United States Patent
Campbell et al.

(10) Patent No.: US 9,031,659 B2
(45) Date of Patent: May 12, 2015

(54) METHOD AND APPARATUS FOR LARYNGEAL ELEVATOR MUSCULATURE REHABILITATION

(75) Inventors: Russell A. Campbell, Coppell, TX (US); Ronda Polansky, Haslet, TX (US); Patrick Lee McAdoo, Jr., Fort Worth, TX (US)

(73) Assignee: Ampcare, LLC, Ft. Worth, TX (US)

( * ) Notice: Subject to any disclaimer, the term of this patent is extended or adjusted under 35 U.S.C. 154(b) by 1108 days.

(21) Appl. No.: 13/021,840

(22) Filed: Feb. 7, 2011

(65) Prior Publication Data

US 2011/0190848 A1  Aug. 4, 2011

Related U.S. Application Data

(63) Continuation of application No. 11/827,484, filed on Jul. 11, 2007, now Pat. No. 7,885,713.

(51) Int. Cl.
*A61N 1/36* (2006.01)
*A61N 1/04* (2006.01)

(52) U.S. Cl.
CPC ............ *A61N 1/3601* (2013.01); *A61N 1/0484* (2013.01)

(58) Field of Classification Search
CPC . A61N 1/0492; A61N 1/0484; A61N 1/0472; A61N 1/0452; A61N 1/0408; A61N 1/0404; A61N 1/04
USPC ........................................ 607/139; 128/848
See application file for complete search history.

(56) References Cited

U.S. PATENT DOCUMENTS

| | | | |
|---|---|---|---|
| 3,025,858 A * | 3/1962 | Browner | 607/71 |
| 3,746,004 A * | 7/1973 | Jankelson | 607/139 |
| 4,167,190 A | 9/1979 | Sorenson et al. | |
| 4,366,815 A | 1/1983 | Broomes | |
| 4,390,023 A | 6/1983 | Rise | |
| 4,411,268 A | 10/1983 | Cox | |
| 4,519,400 A | 5/1985 | Brenman et al. | |
| 4,700,697 A | 10/1987 | Mundell et al. | |
| 4,782,824 A | 11/1988 | Davies | |
| 4,907,602 A | 3/1990 | Sanders | |
| 5,016,647 A | 5/1991 | Sanders | |
| 5,133,354 A | 7/1992 | Kallok | |
| 5,265,624 A | 11/1993 | Bowman | |
| 5,507,718 A | 4/1996 | Kabat | |
| 5,725,564 A | 3/1998 | Freed et al. | |
| 5,891,185 A | 4/1999 | Freed et al. | |
| 5,987,359 A | 11/1999 | Freed et al. | |
| 6,104,958 A | 8/2000 | Freed et al. | |

(Continued)

OTHER PUBLICATIONS

Campbell, R., Plansky, R., McAdoo, R., Deciphering Dysphagia with e-stim, Advance for Directors in Rehabilitation, 64, 67-68 (Nov. 1998).

(Continued)

*Primary Examiner* — Carl H Layno
*Assistant Examiner* — Erin Piateski
(74) *Attorney, Agent, or Firm* — McAfee & Taft, A Professional Corporation (57) ABSTRACT

A device useful in treating decreased laryngeal elevation and for muscle re-education and rehabilitation is provided. The device is suitable for transmitting an electrical stimulus and can comprise a series of electrically conductive fibers oriented at an angle such that the fibers are parallel to muscle fibers of the laryngeal elevated musculature in the submandibular region of a patient.

19 Claims, 4 Drawing Sheets

(56) References Cited

U.S. PATENT DOCUMENTS

| | | | |
|---|---|---|---|
| 6,198,970 | B1 | 3/2001 | Freed et al. |
| 6,484,053 | B2 | 11/2002 | Leelamanit et al. |
| 6,668,834 | B1 | 12/2003 | Zikria |
| 6,770,022 | B2 | 8/2004 | Mechlenburg et al. |
| 6,978,787 | B1 | 12/2005 | Broniatowski |
| 7,039,468 | B2 | 5/2006 | Freed et al. |
| 7,885,713 | B2 | 2/2011 | Campbell et al. |
| 2002/0010495 | A1 | 1/2002 | Freed et al. |
| 2003/0093128 | A1 | 5/2003 | Freed et al. |
| 2004/0220645 | A1 | 11/2004 | Freed et al. |

OTHER PUBLICATIONS

Buchholz, et al. "Adaption, Compensation, Decompensation of the Pharyngeal Swallow"; Gastrointestinal Radiology, 1985; pp. 235-239; vol. 10.; Springer-Verlag.

Larsen, George; "Conservative Management for Incomplete Dysphagia Paralytica"; Arch Phys Med Rehabil, Apr. 1973; pp. 180-185; vol. 54.

Hida, et al; "Effects of Submental Stimulation for Several Consecutive Nights in Patients with Obstructive Sleep Apnoes [sic]"; Thorax; 1994; pp. 446-452; vol. 49.

Freed, et al; "Electrical Stimulation for Swallowing Disorders Cased by Stroke"; Respiratory Care; May 2001; pp. 466-474; vol. 45 No. 5.

Decker, et al; "Functional Electrical Stimulation and Respiration During Sleep"; The American Physiology Society; 1993; pp. 1053-1061.

Suzuki, et al.; "Laryngeal Spasm: A Neurophysiologic Redefinition" AMA Otol; 1977; pp. 150-157; vol. 36.

Miller, et al.; "Speech-Language Pathology and Dysphagia: A Brief Historical Perspective"; Dysphagia; 1993; pp. 180-184; vol. 8; Springer Verlag New York, Inc.

Chi-Fishman, et al.; "Thermomechanical Facilitation of Swallowing Evoked by Electrical Nerve Stimulation in Cats"; Dyshpagia; 1994; pp. 149-155; Springer-Veriag New York, Inc.

Humbert, et al.; "Electrical Stimulation Aids Dysphagia"; The ASHA Leader; Mar. 16, 2004; pp. 1-3.

Humbert, et al.; The effect of Surface Electrical Stimulation on Hyolaryngeal Movement in Normal Individuals as Rest and During Swallowing; J App Physiol; Dec. 2006; pp. 1657-1663; vol. 101.

Miki, et al; "Effects of Submental Electrical Stimulation During Sleep on Upper Airway Patency in Patients with Obstructive Sleep Apnea"; American Review of Respiratory Disease; Nov. 1989; pp. 1285-1289; vol. 140.

* cited by examiner

METHOD AND APPARATUS FOR LARYNGEAL ELEVATOR MUSCULATURE REHABILITATION

CROSS-REFERENCE TO RELATED APPLICATIONS

This application is a continuation of and claims priority from U.S. patent application Ser. No. 11/827,484, entitled "METHOD AND APPARATUS FOR LARYNGEAL ELEVATOR MUSCULATURE REHABILITATION" filed Jul. 11, 2007, and now issued as U.S. Pat. No. 7,885,713, the contents of which are incorporated herein by reference.

BACKGROUND

The current invention generally relates to a method of treating decreased laryngeal elevation. More specifically, this invention relates to the use of a neuro-orthotic device, in combination with electrical stimulation of the submandibular muscles, to treat laryngeal elevator musculature. This invention also relates to muscle re-education and rehabilitation by using a neuro-orthotic device, in combination with electrical stimulation of the submandibular muscles, to stimulate laryngeal elevator musculature.

People with dysphagia have difficulty swallowing, and may also experience pain while swallowing. A commonly encountered functional abnormality in individuals with dysphagia is a decrease in laryngeal elevation. Laryngeal elevation is important in the elongation of the pharyngeal-esophageal sphincter, and assistance with epiglottic closure. Often, the decrease in laryngeal elevation is due to atrophy of the laryngeal elevator musculature.

The use of neuromuscular electrical stimulation (NMES) for dysphagia treatment has gained increased interest over several years. There have been a few investigative studies into NMES treatments of dysphagia. Some previous studies have focused on research methods involving the stimulation of open nerves in animals. Other studies have focused on the use of electrical stimulation with parameters adjusted to initiate the swallow reflex.

In the context of sleep apnea research, some researchers have hypothesized that electrical stimulation may improve laryngeal musculature and thereby decrease apneic episodes. There is, however, an absence of published research combining an orthotic or neuro-orthotic in combination with electrical stimulation to promote laryngeal elevator musculature re-education, rehabilitation, or regeneration.

The existing studies are not necessarily a best option for a therapeutic treatment of decreased laryngeal elevation. An evaluation of these techniques for their significance in swallowing rehabilitation and other treatments centered on the submandibular and pharangyeal regions, shows that the specific parameters and uses vary, and the results for the research have not been consistent.

One difficulty researchers face is finding the proper balance of treatment and therapy to overcome the decrease in laryngeal elevation. Major goals of treatment and therapy include being non-invasive to the patient, preventing disuse atrophy of the muscles, increasing range of motion, re-educating muscle functions, temporarily decreasing spasticity, and increasing local blood circulation.

The present invention, as described herein, is directed to the aforementioned problems, deficiencies and goals.

SUMMARY

One embodiment is a method for muscle rehabilitation of laryngeal elevator musculature comprising placing a patient into a neuro-orthotic device for elevation of the laryngeal elevator musculature and applying a protocol of an electrical stimulus to the submandibular region for a sufficient period of time using a sufficient electrical input.

Another embodiment is a method for non-invasive treatment of laryngeal elevator musculature. The method comprises fitting a prosthetic neuro-orthotic device to a patient, and applying at least one pair of electrodes to the submandibular region of the patient. Once positioned, a repeated pulsing of a pre-determined electrical current is sent through the electrodes. The stimulating of the patient's submandibular region muscles is done for a pre-determined period of time.

Another embodiment of this invention is a method for re-educating the laryngeal elevator musculature of a patient. This method comprises placing a patient into a neuro-orthotic device which aligns the cervical spine of the patient in the orthotic device. The method requires applying at least one transcutaneous electrical muscle stimulator electrode to the patient's submandibular region. The positioning of the patient's submandibular region in the neuro-orthotic orthotic device increases the electrical signal efficiency of the electrode. Once positioned, a protocol is applied which has a sufficient electrical current that is applied for a sufficient period of time. The current further comprises, a sufficient frequency, a sufficient pulse width, a sufficient amplitude, a sufficient ramp period, and a sufficient waveform.

Another embodiment of this invention is a method for muscle rehabilitation of laryngeal elevator musculature. The inventive method comprises fitting a patient into a neuro-orthotic device for treatment. The neuro-orthotic device supports the patient's submandibular region for the treatment. The inventive method is to align a plurality of transcutaneous electrical muscle stimulator electrodes on the patient's submandibular with the neuro-orthotic device. The electrodes are applied and positioned to stimulate the laryngeal elevator musculature. The application of a protocol with a pre-determined pulsed electrical current to the patient for a pre-determined time with a pre-determined electrical input is accomplished.

Another embodiment of this invention is a removable electrode. The electrode comprises a pad, a series of electrically conductive elements affixed to the pad and oriented to align with the submandibular muscle fibers, a protective insulating cover affixed to the electrically conductive elements and the pad, and an electrical lead extending from the pad, which is in electrical communication with the series of electrically conductive elements.

Numerous objects and advantages of the invention will become apparent as the following detailed description of the preferred embodiment is read in conjunction with the drawing, which illustrates such embodiment.

BRIEF DESCRIPTION OF THE DRAWINGS

FIG. 8—Is a table of a strength duration curve.

DETAILED DESCRIPTION

Overview

Muscle re-education, re-generation, and rehabilitation to improve laryngeal elevation using NMES are the primary goals of this inventive method and apparatus. The rationale is that the improved range of motion of the larynx and tongue base retraction during swallowing affects airway protection. This anterior motion of the hyolaryngeal complex is essential to improved swallow function.

Electronic stimulation of muscles has been practiced and is understood for many muscles and muscle groups. Electronic stimulation of the muscles forces a specific muscle or muscle group and often ancillary muscles to react to the stimulus. Electronic stimulation in the present invention is directed to muscle re-education, regeneration and rehabilitation of the laryngeal elevator musculature in order to promote laryngeal elevation, but is not intended to, nor set at such a level, to initiate the swallow reflex.

The use of electronic stimulation to promote laryngeal elevation requires that the correct muscles be exercised. The paired muscles of the mylohyoid, geniohyoid and the anterior belly of the digastric musculature are primarily responsible for anterior and superior movement of the hyoid bone during a swallow. This movement of the hyoid and laryngeal elevation is vital in airway protection during swallowing. The anterior/superior movement of the larynx helps bring the airway safely away from the path of the bolus. Techniques used to accentuate and prolong laryngeal elevation are used as indirect dysphagia treatment. These techniques are based on the anatomical relationship of the hyoid, larynx and cricopharyngeal region.

Using a neuro-orthotic device or orthotic in combination with electronic stimulation of the laryngeal elevator musculature provides greater isolation of the muscles, and allows proper positioning and conduction of the electrodes. A neuro-orthotic device also improves laryngeal elevation while reducing complications associated with disorders and injuries of the central nervous system. Additionally, a neuro-orthotic device places the patient in the proper anatomical position to receive the most efficient electronic stimulation treatment. The neuro-orthotic device also prevents the adverse affect of moisture and saliva contacting the electrodes. Provided that the peripheral nervous system is intact, the protocol of this inventive method and apparatus can be used as an adjunct in the clinical treatment of a variety of neuromuscular and musculoskeletal problems. Neuromuscular electrical stimulation (MMES) used in combination with the electrodes of the present invention and a neuro-orthotic device shows an increase of strength and range of motion, facilitating weak contractions due to upper-motor neuron lesions or disuse atrophy, and to re-educate muscles.

Figure 1:
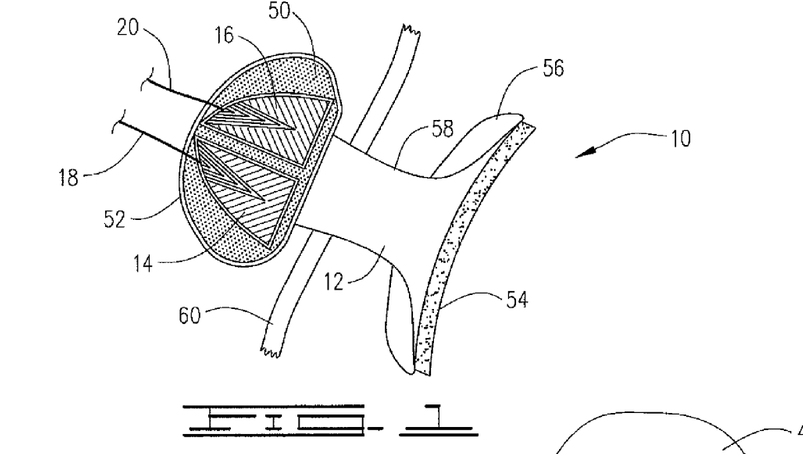
FIG. 1—Is a perspective view of a neuro-orthotic device with the submandibular electrodes placed upon it.

FIG. 1 represents a first preferred embodiment of the invention. Apparatus 10 is the combination of neuro-orthotic device 12 and electrodes 14 and 16. Different variations of apparatus 10 may be created by using a different neuro-orthotic device 12 or different electrodes 14 and 16.

Figure 5:
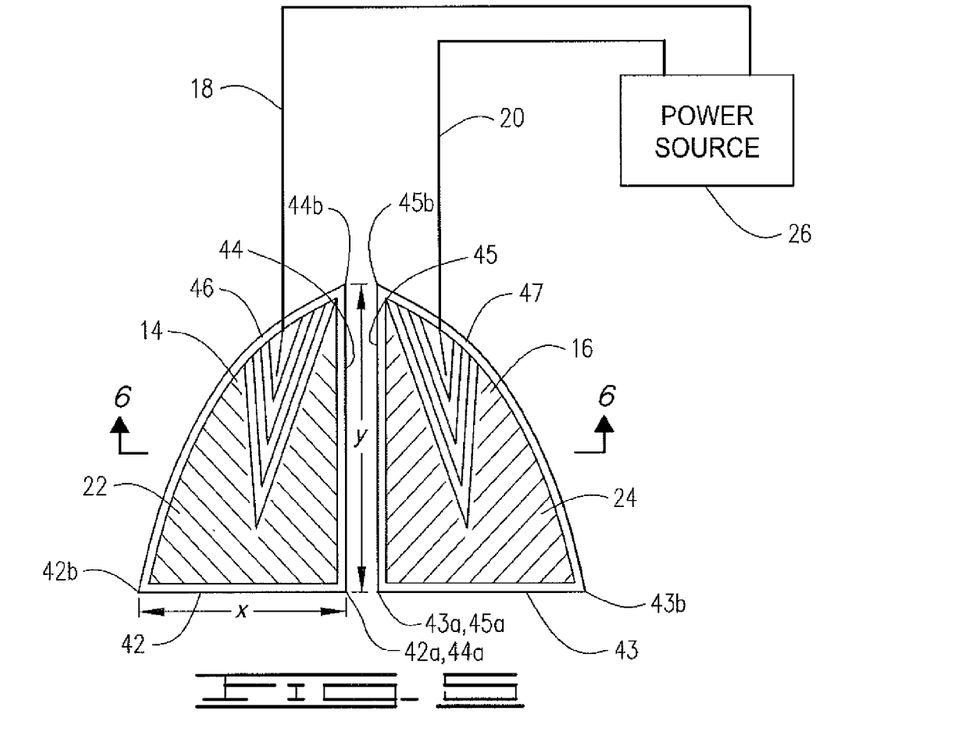
FIG. 5—Is a top view of a set of the inventive electrodes with leads attached.

In FIGS. 1 and 5, electrodes 14 and 16 are shown with electrical leads 18 and 20. Also shown in FIGS. 1 and 5 are conductive elements 22 and 24. Electrical leads 18 and 20 provide electrical current to conductive elements 22 and 24. Electrical leads 18 and 20 are shown in FIG. 5 electrically connected to power source 26. Electrical leads 18 and 20 are shown as separate lines, but they may be combined into a single cable. The electrical current is provided and regulated by power source 26.

Power source 26 is preferably a muscle stimulator capable of providing the protocol parameters described herein. A known power source 26 is the Staodyne EMS+2 manufactured by Compex Technologies, Inc. Other known power sources 26 include the IntelliSTIM BE-28E manufactured by EASYMED Instrument Co. Ltd; Respond Select manufactured by Empi, Inc.; BioStim NMS+ manufactured by Bio-Medical Life Systems, Inc.; and SYS*STIM 26 manufactured by Mettler Electronics Corporation. However, any single or plural power source 26 may be used that substantially meets the protocol requirements of the inventive method described herein.

Figure 6:
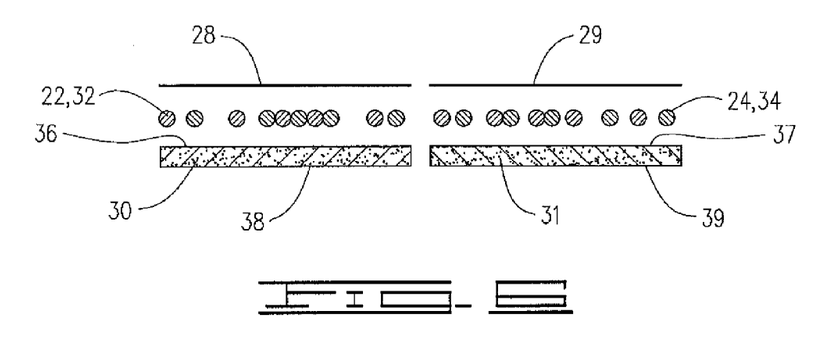
FIG. 6—Is an exploded sectional view of the inventive electrodes taken along section line 6-6 of FIG. 5.

FIG. 6 is an exploded sectional view of electrodes taken along section line 6-6 of FIG. 5. FIG. 6 depicts electrodes 14 and 16 as subcomponents. Conductive elements 22 and 24 are shown positioned between protective insulating covers 28 and 29 and pads 30 and 31. Protective insulating covers 28 and 29 may be any material that is non-conductive and electrically insulating. Preferably, protective insulating covers 28 and 29 are fabricated out of a soft material and also provide a cushion for protection. Conductive elements 22 and 24 are affixed to pads 30 and 31. Conductive elements 22 and 24 are comprised of a series of small fibers 32 and 34. Preferably small fibers 32 and 34 are fabricated out of silver carbon. Preferably, small fibers 32 and 34 are oriented on pads 30 and 31 parallel to the submandibular region 48 muscle fibers when electrodes 14 and 16 are applied to patient 40. Pads 30 and 31 are preferably fabricated out of a material allowing conductive elements 22 and 24 to transmit electrical current with minimal electrical loss. In the preferred embodiment, a gel pad was used for pads 30 and 31.

Pad 30 has pad first side 36 and 37 and pad second side 38 and 39. Conductive elements 22 and 24 are affixed to pad first side 36 and 37. Pad second side 38 and 39 is preferably inherently tacky such that it will stick to patient 40, shown in FIGS. 2 and 7. However, pad second side 38 and 39 may be coated with a tacky substance.

Figure 7:
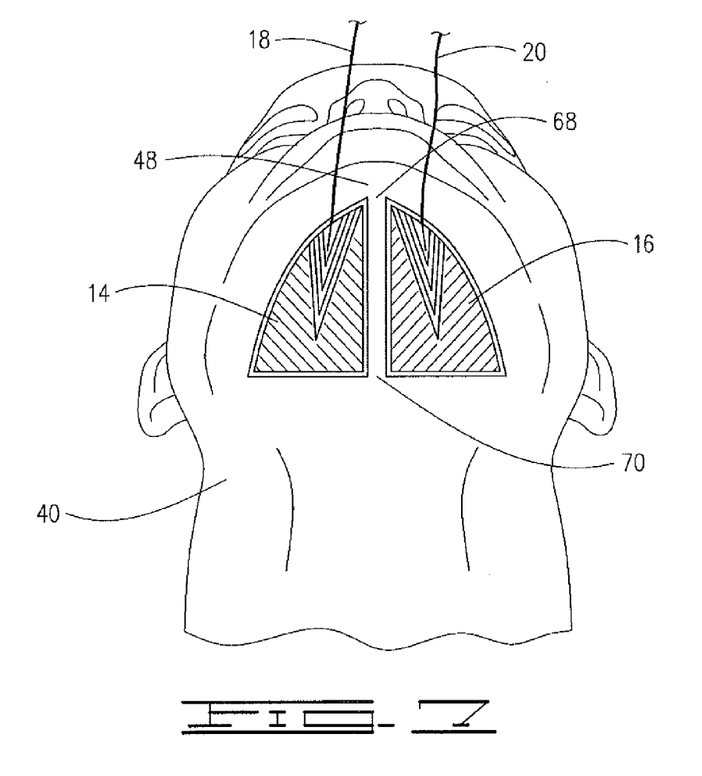
FIG. 7—Is a bottom view of a set of the inventive electrodes affixed to a patient's submandibular region.

Electrodes 14 and 16 are shown in FIGS. 1, 5 and 7 as geometric shaped segments. The geometric shaped segment of electrodes 14 and 16 is designed to conformably place electrodes 14 and 16 on submandibular region 48, and to properly orient small fibers 32 and 34 in relation to the submandibular region 48 muscle fibers. Each segment has first leg 42 and 43 having a length x, and second leg 44 and 45 having a length y connected by arcuate portion 46 and 47. Length "x" and length "y" may be produced in different sizes to meet the needs of differently sized patients 40. For the preferred embodiment, length "x" is about 3.7 centimeters in length. For the preferred embodiment, length "y" is about 4.4 centimeters in length. First leg 42 and 43 has a first leg first end 42a and 43a and a first leg second end 42b and 43b. Second leg 44 and 45 has a first leg first end 44a and 45a and first leg second end 44b and 45b. As seen in FIG. 5, first leg first end 42a and 43a is connected the second leg first end 44a and 45a. Arcuate portion 46 and 47 connects first leg second end 42b and 43b and second leg second end 44b and 45b.

Electrodes 14 and 16 are shown as mirror images of each other, and each is sized to substantially cover one-half of submandibular region 48 of patient 40. FIG. 7 depicts electrodes 14 and 16 positioned upon submandibular region 48 of patient 40. Only electrodes 14 and 16 are shown in FIGS. 1 and 5-7. Electrodes 14 and 16 are preferably used in pairs with a waveform that is biphasic. However, a single electrode 14 or 16 may be used in combination with a form of a manual probe.

Figures 2, 3:
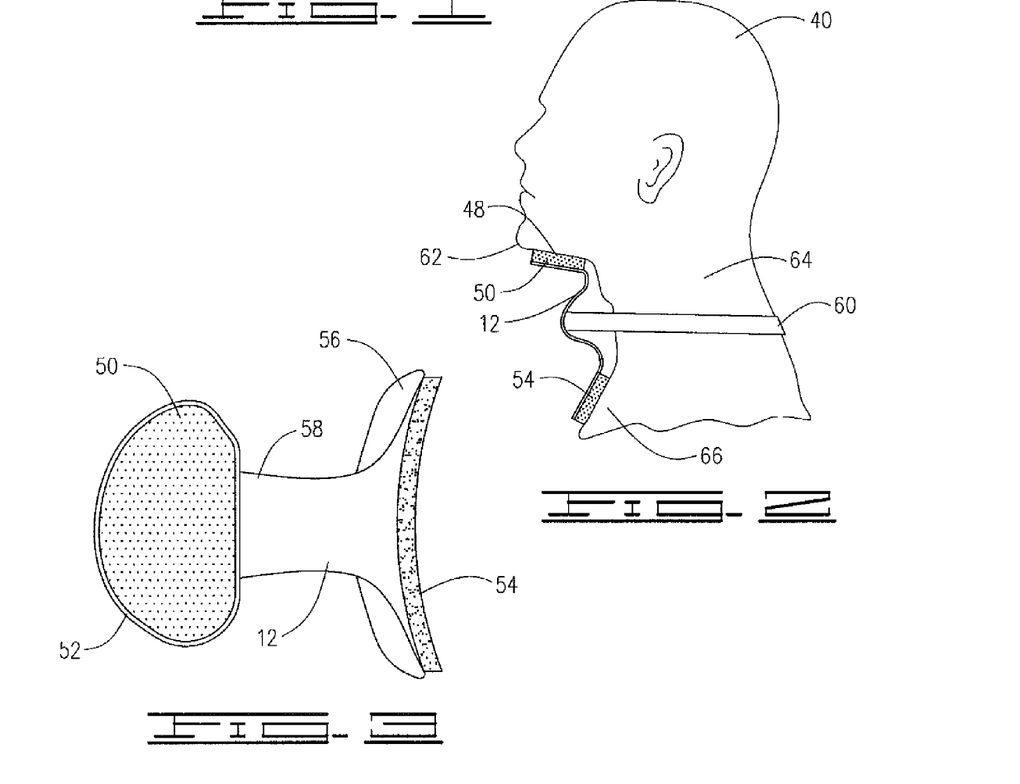
FIG. 2—Is a side elevation view of a neuro-orthotic device.
FIG. 3—Is a top view of a neuro-orthotic device.
Figure 4:
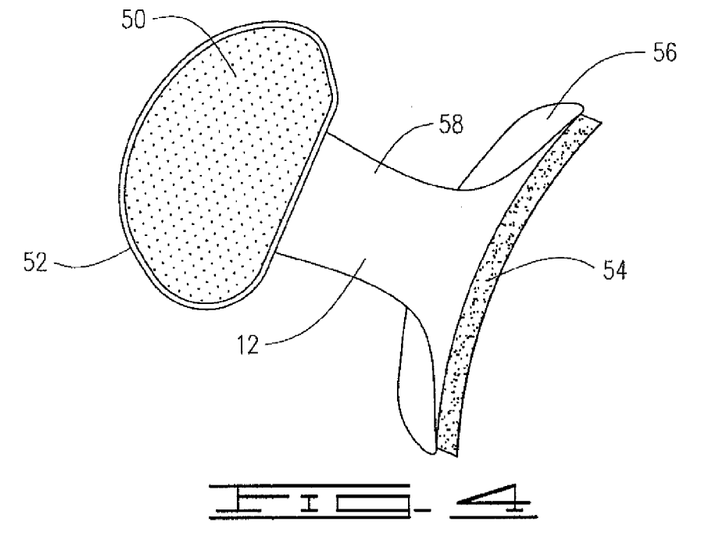
FIG. 4—Is a perspective view of a neuro-orthotic device.

Electrodes 14 and 16 are used in combination with neuro-orthotic device 12. Electrodes 14 and 16 are shown in FIG. 1 positioned upon chin pad 50 of orthotic device 12. Neuro-orthotic device 12 may be any orthotic or neuro-orthotic that properly elevates the laryngeal elevator musculature. The preferred neuro-orthotic device 12 is a device previously marketed as the "REST-EZZZ™ with ESP (Enhanced Swallow Posture)" by Restorative Medical Incorporated headquartered in Brandenburg, Ky. The minimum criteria in selecting neuro-orthotic device 12 are the proper positioning of the laryngeal elevator musculature and non-interference with electrodes 14 and 16. Once properly positioned, as shown in FIG. 2, neuro-orthotic device 12 facilitates anterior and superior hyoidal movement while maintaining proper postural alignment with optimal contact of electrodes 14 and 16. Additionally, neuro-orthotic device 12 facilitates better contact between the submandibular region 48 musculature and electrodes 14 and 16. The better contact is achieved by patient 40 resting chin 62 upon neuro-orthotic device 12, which improves contact with the submandibular region 48 musculature.

FIGS. 1-4 depict the preferred neuro-orthotic device 12. Neuro-orthotic device 12 has chin pad 50, chin pad support structure 52, chest pad 54, chest pad support structure 56, connective support structure 58, and retention strap 60. Chin pad 50 is designed to comfortably support chin 62 of patient 40 without interfering with electrodes 14 and 16 affixed to submandibular region 48.

Referring to FIG. 2, neuro-orthotic device 12 is shown with an ergonomic design to support chin 62 while keeping neuro-orthotic device 12 away from neck 64 of patient 40. Chest 66 of patient 40 is used to provide a fulcrum to support chin 62 with neuro-orthotic device 12. Retention strap 60 is shown around the back of neck 64. In this position, neuro-orthotic device 12 is held in position for treatment. Once positioned, as shown in FIG. 2, the laryngeal elevator musculature of patient 40 is properly positioned for treatment.

Patient 40 is depicted in FIG. 2 as a human. However, this inventive method is applicable to any animal having submandibular region 48. Usage of the term animal is meant to include all human and non-human species having a submandibular region 48.

FIGS. 2 and 7 illustrate a preferred embodiment of the inventive method. In particular, electrodes 14 and 16 are affixed to submandibular region 48 of patient 40. Second leg 44 and 45 of electrodes 14 and 16 are placed along a line between anterior placement point 68 and posterior placement point 70 as shown in FIG. 7. The unique shape of electrodes 14 and 16 ensures the proper alignment of small fibers 32 and 34 in relation to the submandibular region 48 muscle fibers. The placement of electrodes 14 and 16 is preferably non-invasive.

With electrodes 14 and 16 in place, neuro-orthotic device 12 is placed under chin 62 of patient 40. Chin pad 50 of neuro-orthotic device 12 comfortably raises the submandibular region 48 of patient 40 to a proper position. In the proper position, the laryngeal elevator musculature of patient 40 is positioned for the maximum muscle re-education and rehabilitation. Chin pad 50 may be used to align electrodes 14 and 16 for initial treatment and for subsequent treatments, thus ensuring consistent or repeatable placement of electrodes 14 and 16 on submandibular region 48.

A proper protocol is used for treatment of the patient. The application of the proper protocol uses a pre-determined, or sufficient, pulsed electrical current sent through electrodes 14 and 16 for a pre-determined, or sufficient, time with a pre-determined, or sufficient, electrical input. Pre-determined, or sufficient, power comprises a sufficient voltage, a sufficient frequency, a sufficient pulse width, a sufficient amplitude, a sufficient ramp period, and a sufficient waveform. Pre-determination, or sufficiency, is based upon the needs of patient 40 and what is tolerable to patient 40. The application of a sufficient frequency produces a smooth tetanic contraction in the muscles of a submandibular region 48 without causing spasms.

A pre-determined, or sufficient, protocol typically requires treatment twice a day for about 15 minutes. The duty cycle of the protocol starts about 5 seconds on and about 25 seconds off. Once patient 40 can tolerate the treatment, the duty cycle is changed to about 5 seconds on and about 15 seconds off. The maximum duty cycle is about a 1:1 ratio, or about 5 seconds on and about 5 seconds off.

The preferred protocol frequency is about 30 hertz (30 pulses per second). The protocol pulse width is between about 240 microseconds to about 260 microseconds. The preferred initial trial pulse width is about 250 microseconds. However, if patient 40 finds the treatment painful, and is still able to activate sensory and motor recruitment, the pulse width may be lowered between about 40 microseconds to about 60 microseconds. If the pulse width is lowered to between about 40 to about 60 microseconds, the amperage is preferably doubled. The protocol amperage is preferably about 10 milliamps to about 80 milliamps. However, the amperage is tied to the pulse width for maximum muscle stimulation. The amplitude is between about 10 milliamps to about 40 milliamps for a pulse width of about 250 microseconds. The amplitude is between about 30 milliamps to about 80 milliamps for a pulse width of about 50 microseconds. The protocol uses pulsed current. In one clinical trial the amplitude had a range of 14 milliamps to 35 milliamps for an input voltage range of 11 millivolts to 100 millivolts. The average was 18.72 milliamps and 46.04 millivolts. The protocol ramp, or rise in intensity, is about 0.4 seconds. The waveform of the protocol is preferably a symmetrical biphasic waveform when pairs of electrodes 14 and 16 are utilized.

To stimulate the anterior digastric and mylohyoid muscles, the current must pass through the skin/fascia layer and platysma. The electrical current passes through these layers to the anterior digastric and mylohyoid musculature, and may overflow into other musculature such as the geniohyoid and hyoglossus. The benefits of stimulating this region are that they voluntarily assist the depression of the tongue via the hyoglossus and contract the digastric muscles, mylohyoid and geniohyoid muscles assisting in the anterior/superior movement of the larynx.

The goal of using these preferred parameters of the protocol is for re-educating the laryngeal elevator musculature without inducing a swallow reflex. To accomplish this goal, the anterior digastric muscle, which originates on the inferior border of the mandible, is stimulated since it is the most superficial suprahyoidal muscle. The anterior digastric muscle insertion at the cornu of the hyoid acts to elevate and pull the hyoid anteriorly. The stimulation overflows to the mylohyoid for its origin on the mylohyoid line of the mandible and its insertion at the body of the hyoid, which acts to elevate and pull the hyoid anteriorly. The stimulation overflows to the hyoglossus for its origin on the hyoid bone and its insertion at the sides of the tongue which depresses the tongue. The stimulation may overflow to the geniohyoid which is depresses the jaw and elevates and protracts the hyoid. Origin of the geniohyoid from the inferior mental spine on the back of the symphysis menti and inserts to the hyoid bone.

Using a pulse rate of about 30 Hertz produces a tetanizing muscle contraction with minimal muscle fatigue and without causing spasm. Tetanizing is a condition characterized by twitching/contracting muscles. Using a pulse width of about 250 microseconds increases the depth of penetration of the current. Initial trial of 250 microseconds is recommended to achieve muscle tetany. The higher the pulse width, the greater the penetration of current and the lower the intensity needed to make a contraction. The lower the pulse width, the shallower the penetration of current and the higher the intensity needed to make a contraction. The strength duration curve provided in FIG. 8 indicates that the large sensory nerves are activated first, motor nerves are activated second, and pain nerves are activated third.

The higher the amplitude, the greater the increase in the number of muscle motor units activated. The preferred amplitude is patient variable, ranging from 10 milliamps to 100 milliamps which is sufficient to elicit a comfortable motor/tetanic response in patient 40. Ramp up time, or ramp time, is the length of time it takes for the output stimulus to reach maximum strength for each muscle contraction. The ramp time aids in the comfort of the treatment. Typically, a ramp time of 0.4 seconds can be used to mimic normal recruitment and is suggested for the comfort of patient 40.

The duty cycle affects the fatigue rate of patient 40. Depending upon patient 40, initial treatments for muscle re-education may require longer on/off time in the duty cycle. A duty cycle of about 1:3, about 5 seconds on and about 15 seconds off, is typically less fatiguing to patient 40. However, it is recommended that treatment start at a duty cycle of about 1:5, about 5 seconds on and about 25 seconds off. The maximum duty cycle is about 1:1, about 5 seconds on and about 5 seconds off.

The preferred waveform is a symmetrical biphasic waveform. The symmetrical biphasic waveform efficiently stimulates both electrodes 14 and 16. The size and placement of electrodes 14 and 16 must be chosen such that they provide the desired response for patient 40 avoiding the carotid sinus. Any power source 26 that is a powered muscle stimulator labeled for "muscle re-education" can be used with neuro-orthotic device 12 as long as it is capable of meeting the protocol parameters and follows the manufacturers listed contraindications.

The neuro-orthotic device 12 positions submandibular region 48 of patient 40 into a position such that the laryngeal elevator muscles are stimulated without inducing a swallowing action. This movement facilitates patterns leading to the reversal of disuse atrophy, while improved posture will enhance the ability to breathe and take in nutrition and hydration. Neuro-orthotic device 12 comfortably embraces submandibular region 48, and can be used as an orthosis to decrease pain from poor posture. An additional benefit is that this inventive method should increase the quality of life as patients will be able to take part in activities which may also improve their degree of orientation and cognition. Preferably, neuro-orthotic device 12 can be customized to allow for accurate and easy application/removal. By using heavy gloves and moving a heat gun in a small circular motion, neuro-orthotic device 12 can be remolded to change the angle of chin pad support structure 52 or chest pad support structure 56 to lengthen or shorten the overall height.

In a multi-center prospective clinical trial study, the principles of this invention were applied to a real world setting, using the protocol shown below on long term care patients who exhibited dysphagia due in part to poor or diminished laryngeal elevation. The time of each treatment included two 15-minute sessions daily, for a total of 30 minutes of therapy time. This protocol is accomplished 5 times per week.

The evaluated patients were from multiple long term care facilities in Texas. Group 1 included patients receiving at least 20 therapy days of the Neuromuscular Electrical Stimulation (NMES) protocol as well as traditional therapy (59 patients). Group 2 included patients receiving traditional dysphagia therapy only, as would have been performed prior to any NMES modality training, or for patients who refused the NMES therapy protocol (46 patients).

A total of 105 patients were evaluated with the Modified Barium Swallow Study (MBSS) by a trained licensed speech language pathologist, and were found to have impaired laryngeal elevation as a primary or secondary dysfunction causing aspiration or risk of aspiration to the degree that diet changes were necessary. A swallow severity scale was established to determine the diet after the initial diagnosis of dysphagia using fluoroscopy. The subset of patients who were able to tolerate at least 20 days of traditional dysphagia therapy while also using the NMES established protocol were included in the analysis as patients having successful completion of the protocol. A comparison was made from a total of 46 patients who received only the traditional dysphagia therapy, but whose chart reviews noted these patients exhibited dysphagia with decreased laryngeal elevation as diagnosed from an MBSS. These charts were evaluated as to the number of patients who had an improved swallow severity scale. The severity scale is shown in Table 1.

TABLE 1

Severity Scale

| | |
|---|---|
| 0 - | NPO |
| 1 - | Therapeutic intake only. |
| 2 - | Pleasure feedings only, unsupervised >2-3 times per day. |
| 3 - | Modified diet of either thickened liquids, puree or mechanical soft with strategies (3 meals/day). |
| 4 - | Strategies only, no alternate method of intake. |
| 5 - | Normal swallow function. |

The results of the study were promising. The swallow severity scale improved from a 2.25 level to a 3.6 level in the NMES subgroup receiving at least 20 days of the NMES protocol. The swallow severity scale improved from a 2.52 level to a 2.60 level in the traditional therapy group. A review of patients' charts revealed that not all of the patients were able to achieve a period of at least 20 days in the traditional therapy group. The average number of therapy visits in the NMES subgroup was 37.71 visits (range: 20-91). The average number of therapy days in the traditional study group was 19 days (range: 8-44). In this study, 59% of the patients who received at least 20 days of the NMES protocol had a diet upgrade, while 41% of the patients did not improve in diet upgrades. It should be noted that 4 patients were already at a high swallow rating prior to beginning therapy (mechanical soft with thin liquids), and therefore did not have much room to improve. In the traditional therapy arm of this review, 10% of patients improved to achieve a diet upgrade, 80% of the patients did not improve to a diet upgrade, and 10% of the patients had a decline in ability. There were no significant adverse events that occurred during this study period. There were some patients who refused therapy both with the NMES, as well as the traditional methods. Some patients were discharged back to a hospital with ongoing medical illnesses which were not attributed to either therapy group. Most of these patients did not meet the intent to treat criteria of 20 days of the NMES therapy protocol.

The results of this clinical trial suggest that patients who present with dysphagia due in part to diminished laryngeal elevation and receive NMES to the laryngeal elevators as an adjunct to traditional methods of therapy improved in diet upgrades and swallow function at a higher percentage as compared to those patients who did not receive the NMES protocol. There were also more than 4,200 therapy visits using this protocol in this study, which would suggest that it is a safe adjunct to include in treating pharyngeal dysphagia with impaired laryngeal elevation. It was also evident, that due to the continued progress over weeks of NMES therapy, speech treatment was ongoing (ranging from 2-3 months). This was compared to earlier discharge from therapy (within 4-6 weeks) due to lack of progress noted with traditional therapy only.

Therefore, it will be seen that the apparatus and method of the present invention are well adapted to carry out the ends and advantages mentioned, as well as those inherent therein. While a presently preferred embodiment of the apparatus and method have been described for the purposes of this disclosure, numerous changes in the arrangement and construction of parts in the apparatus, and steps in the method may be made by those skilled in the art. All such changes are encompassed within the scope and spirit of the appended claims.

What is claimed is:

1. A device for transmitting an electrical stimulus comprising:
   a pair of electrodes, each electrode having a geometric shape defined by a first leg having a first length, a second leg having a second length, wherein a first end of the first leg and a first end of the second leg are connected, and an arcuate portion connecting a second end of the first leg with a second end of the second leg, wherein each electrode comprises a series of electrically conductive fibers oriented at an angle relative to the second leg, wherein the angle is parallel to muscle fibers of laryngeal elevator musculature in a patient's submandibular region when the second leg is oriented parallel and adjacent to a median anterior-posterior plane dividing the submandibular region.

2. The device of claim 1, wherein the first leg is perpendicular relative to the second leg.

3. The device of claim 1, wherein the first length is about 3.7 centimeters and wherein the second length is about 4.4 centimeters.

4. The device of claim 1, wherein the first length and second length are sufficient for each electrode to cover a substantial portion of one-half of the submandibular region of the patient.

5. The device of claim 1, wherein each electrode further comprises:
   a pad;
   the series of electrically conductive elements affixed to said pad;
   a protective insulating cover affixed to said electrically conductive elements and said pad; and,
   an electrical lead connected to said series of electrically conductive elements.

6. The device of claim 1, wherein the geometric shape of each electrode conformable to an anatomical shape provided by a half-portion of the submandibular region of the patient, the submandibular region having an anterior and a posterior and wherein the half-portion is one of two equal portions divided by a median plane that extends from the anterior to the posterior of the submandibular region.

7. A device for transmitting an electrical stimulus comprising
   a pair of electrodes, each electrode having a geometric shape defined by a first leg having a first length, a second leg having a second length, wherein a first end of the first leg and a first end of the second leg are connected, and an arcuate portion connecting a second end of the first leg with a second end of the second leg; and
   a neuro-orthotic support assembly, the neuro-orthotic support assembly comprising:
      a chin support;
      a chest support;
      a connective support structure connecting said chin support to said chest support; and
      a retention strap attached to said connective support structure.

8. The device of claim 7, further comprising an electrical lead connected to a series of electrically conductive elements in each electrode; and
   a power source, wherein the power source provides an electrical current to said series of electrically conductive elements via the electrical lead.

9. The device of claim 8, wherein the electrical current comprises:
   a pulse width from about 240 microseconds to about 260 microseconds; and
   an amperage from about 10 milliamps to about 40 milliamps.

10. The device of claim 8, wherein the electrical current comprises:
    a pulse width from about 40 microseconds to about 60 microseconds; and
    an amperage from about 30 milliamps to about 80 milliamps.

11. A device for transmitting an electrical stimulus comprising:
    a pair of electrodes, each electrode having a geometric shape defined by a first side portion having a first length, a second side portion having a second length, wherein a first end of the first side portion and a first end of the second side portion are connected, and an arcuate portion connecting a second end of the first side portion with a second end of the second side portion, and wherein the first side portion is perpendicular relative to the second side portion and wherein each electrode comprises a series of electrically conductive fibers oriented at an angle relative to the second side portion, wherein the angle is parallel to muscle fibers of laryngeal elevator musculature in a patient's submandibular region when the second side portion is oriented parallel and adjacent to a median anterior-posterior plane dividing the submandibular region.

12. The device of claim 11, further comprising:
    an electrical lead connected to a series of electrically conductive elements in each electrode; and
    a power source, wherein the power source provides an electrical current to said series of electrically conductive elements via the electrical lead.

13. The device of claim 11, wherein the first length is about 3.7 centimeters and wherein the second length is about 4.4 centimeters.

14. The device of claim 11, wherein the first length and second length are sufficient for each electrode to cover a substantial portion of one-half of the submandibular region of the patient.

15. The device of claim 11 further comprising a neuro-orthotic support assembly, the neuro-orthotic support assembly comprising:
    a chin support;
    a chest support;
    a connective support structure connecting said chin support to said chest support; and a retention strap attached to said connective support structure.

16. A device for transmitting an electrical stimulus comprising:
- a pair of electrodes, each electrode having a geometric shape comprising a first leg having a first length, a second leg having a second length, wherein a first end of the first leg and a first end of the second leg are connected and wherein the first leg is perpendicular relative to the second leg, and an arcuate portion connecting a second end of the first leg with a second end of the second leg; and
- wherein each electrode comprises a series of electrically conductive fibers oriented at an angle relative to the second leg, wherein the angle is parallel to muscle fibers of laryngeal elevator musculature in a patient's submandibular region when the second leg is oriented parallel and adjacent to a median anterior-posterior plane dividing the submandibular region; and
- wherein the first length and second length are sufficient for each electrode to cover a substantial portion of one-half of the submandibular region of the patient.

17. The device of claim 16 further comprising a neuro-orthotic support assembly, the neuro-orthotic support assembly comprising:
- a chin support;
- a chest support; and
- a connective support structure connecting said chin support to said chest support.

18. A device for transmitting an electrical stimulus comprising:
- an electrode having a side portion and a series of electrically conductive fibers oriented at an angle relative to the side portion, wherein the angle is parallel to muscle fibers of laryngeal elevator musculature in a patient's submandibular region when the side portion is oriented parallel and adjacent to a median anterior-posterior plane dividing the submandibular region.

19. The device of claim 18, further comprising:
- an electrical lead connected to the series of electrically conductive fibers in said electrode; and
- a power source, wherein the power source provides an electrical current to said series of electrically conductive fibers via the electrical lead.

* * * * *